United States Patent [19]

Ito

[11] Patent Number: 4,487,693
[45] Date of Patent: * Dec. 11, 1984

[54] MULTI-LAYER COIL COUNTERCURRENT CHROMATOGRAPH WITH ADJUSTABLE REVOLUTIONAL RADIUS

[75] Inventor: Yoichiro Ito, Bethesda, Md.

[73] Assignee: The United States of America as represented by the Department of Health and Human Services, Washington, D.C.

[*] Notice: The portion of the term of this patent subsequent to May 18, 1999 has been disclaimed.

[21] Appl. No.: 554,795

[22] Filed: Nov. 23, 1983

Related U.S. Application Data

[63] Continuation-in-part of Ser. No. 416,107, Sep. 9, 1982.

[51] Int. Cl.³ .............................................. B01D 15/08
[52] U.S. Cl. .................................. 210/198.2; 210/657
[58] Field of Search ............................... 210/657, 198.2

[56] References Cited

U.S. PATENT DOCUMENTS 4,430,216 2/1984 Ito .................................... 210/198.2

Primary Examiner—John Adee
Attorney, Agent, or Firm—Browdy and Neimark

[57] ABSTRACT

A flow-through apparatus for two-phase countercurrent chromatography consisting of a multi-layer helically coiled column carried on a flanged reel mounted on a frame revolving on a first axis. The reel rotates on a second axis parallel to and spaced from the first axis, at the same angular velocity and in the same direction as the frame to prevent twisting of its inlet and outlet flow tubes, which extend through an axial passage in a shaft portion of the reel. The reel has opposite shaft portions which are journalled in detachable opposite bearing blocks carried by the frame. The bearing blocks have a plurality of sets of bearings spaced to define different spaced positions of the second axis relative to the first axis, enabling adjustment of the $\beta$ value for the system as required. A counterweight is detachably mounted on the frame opposite the multi-layer coiled column by means of detachable supporting blocks, enabling the counterweight to be readily replaced as required by the $\beta$ adjustment.

12 Claims, 2 Drawing Figures

MULTI-LAYER COIL COUNTERCURRENT CHROMATOGRAPH WITH ADJUSTABLE REVOLUTIONAL RADIUS

This is a continuation-in-part of the application of Yoichiro Ito, "High Speed Preparative Countercurrent Chromatography with a Multiple Layer Coiled Column", Ser. No. 416,107, filed Sept. 9, 1982.

FIELD OF THE INVENTION

This invention relates to continuous countercurrent chromatography systems, and more particularly to a system for continuous countercurrent chromatography which employs a multi-layer coiled helical tubular array rotating on its longitudinal axis.

BACKGROUND OF THE INVENTION

The present invention is intended to perform an efficient countercurrent chromatography for separation of macromolecules and other materials by multi-layer coil planet centrifugation. The present invention is an improvement on the device of U.S. patent application Ser. No. 416,107 and it also relates to prior art such as shown in U.S. Pat. No. 4,228,009, entitled "Toroidal Coil Planet Centrifuge".

In U.S. patent application Ser. No. 416,107, the coil planet centrifuge holds a multi-layer coil which is subjected to a particular type of synchronous planetary motion, i.e., one rotation around its own axis during one revolution around the central axis of the apparatus in the same direction. As described earlier in said prior patent application, this planetary motion establishes a hydrodynamic equilibrium between two immiscible solvent phases in the coiled column which can be efficiently utilized for performing countercurrent chromatography. In this countercurrent chromatographic scheme, rotation of the coil contributes to stabilizing the stationary phase in the coil while the revolution of the coil produces mixing of the two phases to promote partition processing of solutes. In order to achieve the best results, these two effects should be optimized to yield a satisfactory retention level of the stationary phase and at the same time an efficient mixing of the two phases in the coil. Because of the nature of the synchronous planetary motion of the coil applied in this scheme, this optimization is most conveniently carried out by adjusting the ratio $\beta$ between the rotation radius r (distance between the center of rotation and a point on the holder) and the revolutional radius R (distance between the center of revolution and the center of rotation), or $\beta = r/R$. The apparatus described in U.S. application Ser. No. 416,107 has a stationary shaft which extends along the central axis of the apparatus. Under this design of the apparatus, the rotational radius r becomes limited to be always smaller than the revolutional radius R, or to $\beta$ being smaller than 1. Two-phase solvent systems useful for separation of macromolecules often have particular physical properties such as an extremely lower interfacial tension, high viscosity, and small difference in density between the two phases. Such solvent systems exhibit a high tendency of emulsification in the coiled column and may not be applicable to countercurrent chromatography in the present scheme unless the $\beta$ of the system is made substantially greater than 1.

SUMMARY OF THE INVENTION

The present invention eliminates the use of the central shaft and provides large $\beta$ values of the coiled column by reducing the revolutional radius of the holder. Consequently, this design permits application to low interfacial tension phase systems for separations of macromolecules.

As mentioned earlier, the present invention is also related to the device of U.S. Pat. No. 4,228,009, a toroidal coil planet centrifuge apparatus which provides an identical type of synchronous planetary motion for the column holder. This prior apparatus employs an entirely different type of coiled column (the toroidal coil) to carry out analytical-scale separations. Although the $\beta$ value of this prior art centrifuge can be made greater than 1 by eliminating the use of the central shaft, it is not adjustable according to the need for application to various types of solvent systems. In addition, the coil holder of the toroidal coil planet centrifuge is not adaptable for the use of a multi-layer coil because the holder is not made removable from the rotary frame for preparation of the column.

Accordingly, a main object of the invention is to provide an improved countercurrent chromatography system which overcomes the deficiencies and disadvantages of the previously employed countercurrent chromatography systems.

A further object of the invention is to provide an improved countercurrent chromatography system which is adjustable to provide for application to various types of solvent systems.

A still further object of the invention is to provide an improved countercurrent chromatography system using a multi-layer coiled column wherein high $\beta$ values of the coiled column can be provided by reducing the revolutional radius of the coil holder, permitting application to low interfacial tension phase systems for separations of macromolecules.

A still further object of the invention is to provide an improved countercurrent chromatography system employing a coiled column rotatably mounted on a revolving frame, wherein the column is readily removable from the revolutional frame and can be adjusted in position to provide a desired $\beta$ value of the coiled column.

A still further object of the invention is to provide an improved countercurrent chromatography system employing a multi-layer coiled column rotatably mounted on a revolving frame wherein the column may be selectively mounted on the frame at a desired radial distance from the axis of revolution of the frame, whereby to obtain a desired value of $\beta$ for the system.

A still further object of the invention is to provide an improved countercurrent chromatography system employing a coiled column rotatably mounted on a revolving frame by means of bearing blocks which may be readily detached for changing the position of the rotary axis of the column or for replacing the bearing blocks to provide the desired positioning of the column, relative to the revolutional axis of the column.

BRIEF DESCRIPTION OF THE DRAWINGS

Further objects and advantages of the invention will become apparent from the following description and claims, and from the accompanying drawing, wherein:

DETAILED DESCRIPTION OF A PREFERRED EMBODIMENT

Figure 1:
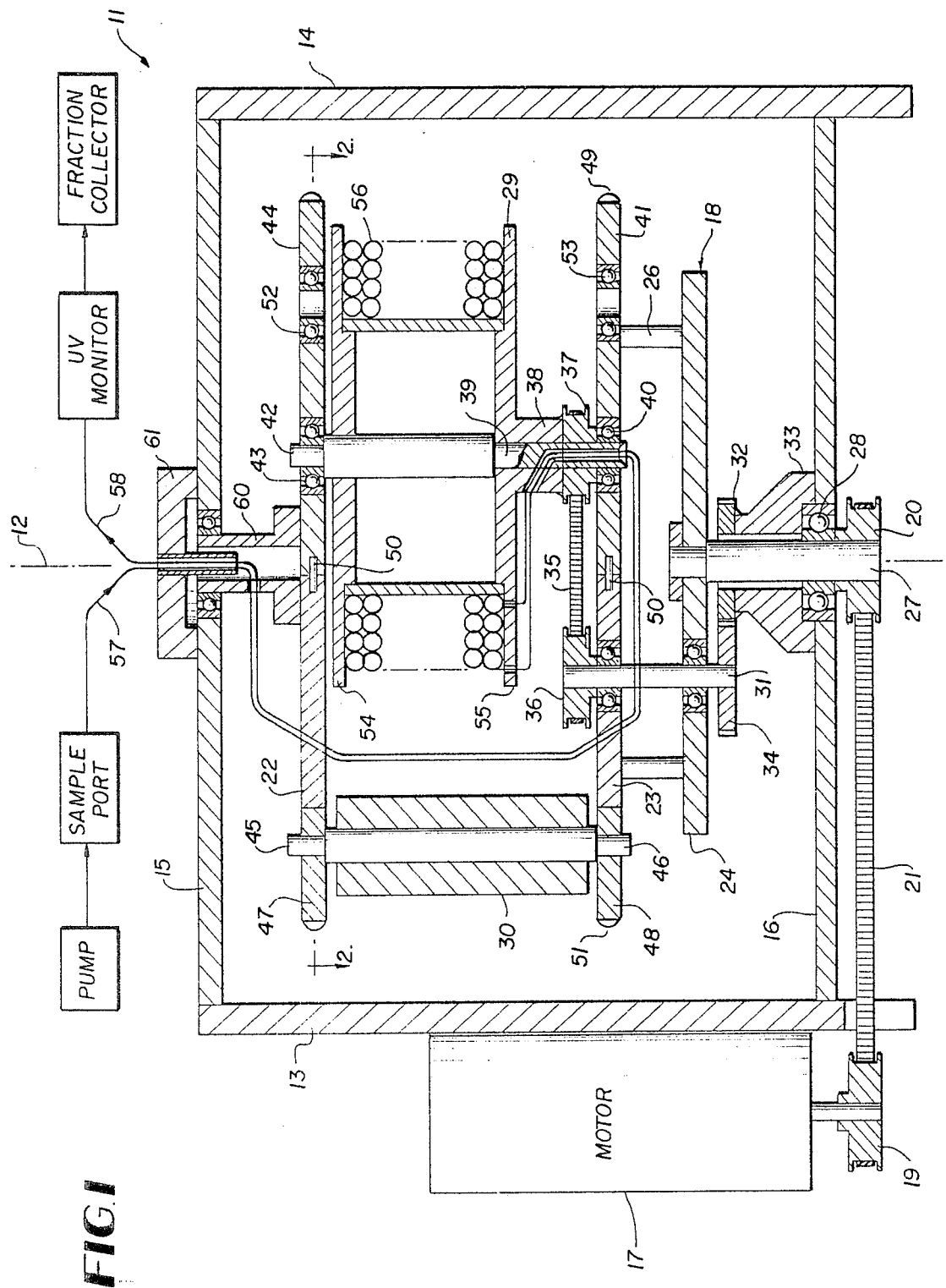
FIG. 1 is a partly diagrammatic vertical cross-sectional view of an improved countercurrent chromatography apparatus constructed in accordance with the present invention.

Referring to the drawings, 11 generally designates an improved countercurrent chromatography apparatus according to the present invention. The apparatus 11 comprises a supporting housing including opposite vertical end walls 13, 14 rigidly connected by a horizontal top wall 15 and a horizontal bottom wall 16. A motor 17 mounted on end wall 13 drives a rotary frame 18 by means of a pair of toothed pulleys 19, 20 and a toothed belt 21.

The rotary frame 18 consists of three horizontal aluminum plates 22, 23 and 24 rigidly linked together by plurality of vertical link bars. Thus, the plates 22, 23 are rigidly connected by a plurality of spaced link bars 25 (FIG. 2), and the plates 23, 24 are rigidly connected by a plurality of spaced link bars 26 (FIG. 1).

The rotary frame 18 is rotatably supported with respect to bottom wall 16 by the vertical shaft 27 carrying the toothed pulley 20, by means of a suitable bearing assembly 28. The rotary frame 18 supports three elements: (1) a column holder 29, (2) a removable counterweight 30, and (3) a vertical countershaft 31. Rotation of the frame 18 develops a planetary motion of the countershaft 31 by means of gear coupling between a stationary gear 32 axially mounted on an upstanding annular support 33 secured on bottom wall 16, and an identical planetary gear 34 mounted on the bottom end of countershaft 31. This motion of countershaft 31 is transmitted to the column holder 29 by 1:1 pulley coupling via a toothed belt 35, a toothed driving pulley 36 on countershaft 31, and a driven toothed pulley 37 secured on the bottom hub portion 38 of holder 29.

Column holder 29 has a bottom shaft portion 39 journalled in a bearing 40 provided in a bottom bearing block 41 removably secured in plate member 23, and has a top shaft portion 42 journalled in a bearing 43 provided in a top bearing block 44 removably secured in top plate member 22.

Since the motion of the countershaft 31 is conveyed to the column holder 29 by the 1:1 ratio pulley coupling provided by toothed belt 35, the holder 29 undergoes a desired synchronous motion, that is, rotation around its own axis and revolution around the central axis 12 of the centrifuge at the same angular velocity and in the same direction.

Figure 2:
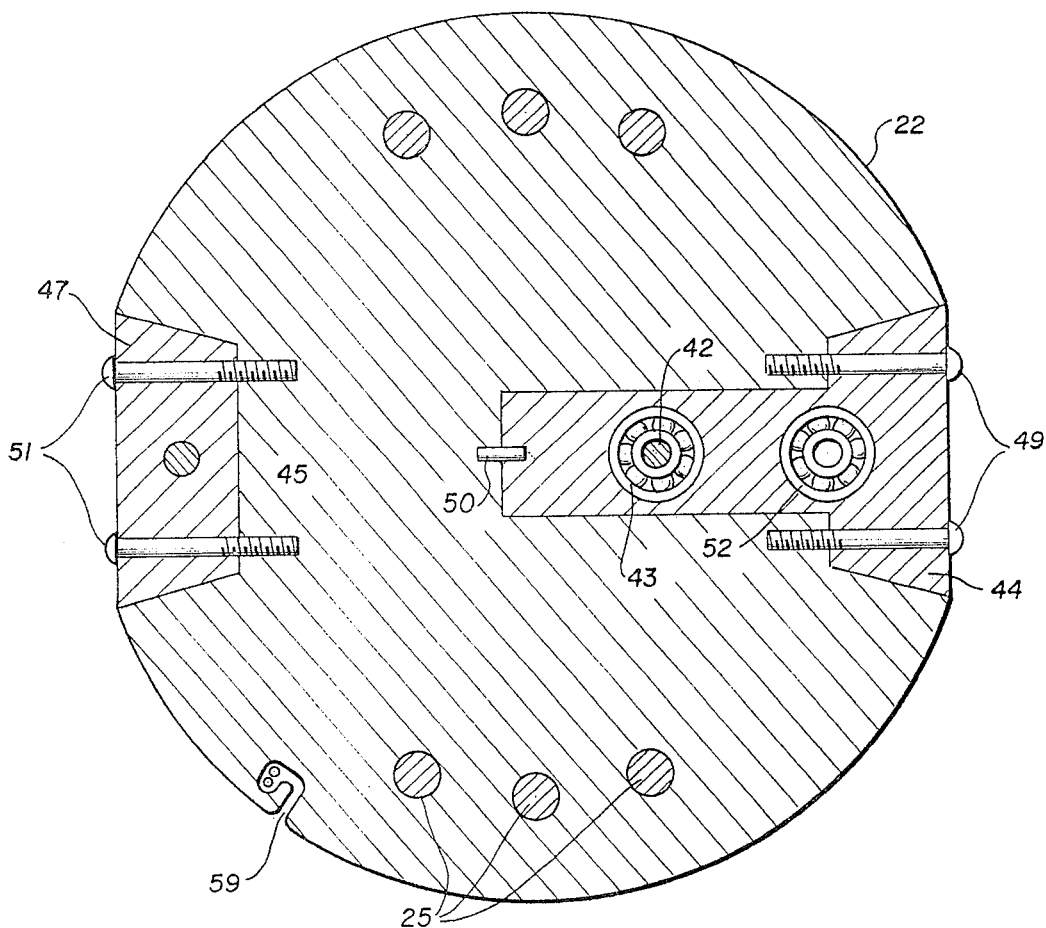
FIG. 2 is a horizontal cross-sectional view taken substantially on line 2—2 of FIG. 1.

The counterweight 30 has top and bottom shaft portions 45, 46 retentively received in removable insert blocks 47, 48 provided in plate members 22 and 23. As shown in FIG. 2, the column holder bearing blocks are generally T-shaped and are removably secured in place by fastening screws 49, 49 and cooperating guide pins 50. The counterweight insert blocks 47, 48 are generally trapezoidal in shape and are removably secured in place by fastening screws 51, 51.

Both the column holder bearing blocks 44, 41 and the counterweight blocks 47, 48 can be removed by loosening their fastening screws 49, 51. The bearing blocks 44, 41 for supporting the column holder have two sets of bearings, 43, 40 and 52, 53 to accommodate the holder at two different radially spaced positions relative to axis 12. The pin 50 mounted at the inner end edge of each bearing block supports the block in proper position on the rotary frame 18. Various $\beta$ values for the coil holder 29 (various positions of the holder) can be provided by using different sets of blocks, with their bearings at the desired positions and employing a suitable timing belt 35 for coupling the pulley 37 on the holder to the pully 36 on the countershaft 31.

The column holder 29 is generally spool-shaped, with a pair of large flanges 54, 54 to accommodate a multi-layer coiled column 56. The column is made from a single piece of PTFE tubing, which may have a desired internal diameter and length, by winding it around the holder between the flanges 54, 55 to produce a reel-like configuration. The inlet and outlet flow tubes are shown respectively at 57, 58. The flow tubes are passed through holes in flange 55 and then through a central passage in the holder shaft portion 39 to reach the space between the plate members 23, 24 of the rotary frame 18. Then the flow tubes are brought to the peripheral portion of the rotary frame and are retentively engaged through hook-shaped retaining slots 59 (FIG. 2) in the peripheral portions of the plate members 23 and 22. The flow tubes are finally passed through a side hole of a short, vertical, upstanding coupling pipe 60 centrally secured to plate member 22 and journalled in top wall 15, and are engaged supportingly through a stationary tube support 61 extending downwardly from the top wall member 15. This arrangement, combined with the synchronous planetary motion of the holder 29, prevents twisting of the flow tubes 57, 58 and thus eliminates the need for rotary seals.

In each separation operation, the column 56 is first filled with the stationary phase which is pre-equilibrated with the mobile phase. Then, the sample solution is injected through the sample port, followed by elution of the mobile phase while the apparatus is run at the optimum revolutional speed. The eluate from the outlet tube 58 of the column is continuously monitored with a UV monitor and fractionated into test tube with a fraction collector.

In operation, the apparatus is driven so that the column is rotated always in such a direction that the inner terminal (the end of the coil located closest to the holder axis) of the multi-layer coil becomes the head and the outer terminal (the end of the coil located near the periphery of the holder) becomes the tail. When the mobile phase is the lower (heavier) phase, both sample and the mobile phase should be introduced through the head terminal of the coil, and vice versa. In this way more stationary phase is retained in the multi-layer coiled column to produce better resolution of the solute peaks.

If the retention of the stationary phase is found to be low (less than 30% of the total column capacity) and/or continuous carryover of the stationary phase is observed, the position of the holder axis is adjusted to be closer to the central axis 12 of the apparatus (reduction of the revolutional radius R for improvement of the retention) until a satisfactory retention level is obtained. If the retention level is high but the peak resolution is not sufficient, the position of the holder is moved away from the central axis 12 of the apparatus (increase of the revolutional radius R for promoting the mixing process) to produce better partition efficiency. Flow rate and the revolutional speed of the apparatus are also usable to optimize the retention and partition efficiency for separation.

"Moving the position of the holder" may consist, for example, of shifting the holder 29 from one set of bearings 43, 40 to the other set of bearings 52, 53, or vice versa, for a given set of bearing blocks 44, 41, or changing to another set of bearing blocks providing the desired rotational position of the holder. The counterweight 30 may be similarly changed in position or mass to provide the required balance in accordance with the selected positioning of the holder 29, since the counterweight bearing blocks 47, 48 are readily removable and replaceable.

While a specific embodiment of an improved countercurrent chromatography apparatus has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. An apparatus for continuous countercurrent chromatography comprising a support, frame means rotatably mounted on said support for rotation on a first axis, multi-layer helically coiled separation column means having opposite axial end portions and being rotatably mounted on said frame means for rotation on a second axis parallel to and spaced from said first axis, inlet and outlet flow tubes connected to the terminal ends of said multi-layer helically coiled column means, means to simultaneously revolve said frame means around said first axis and rotate said column means around said second axis, and means carried by said frame means enabling changing the spacing distance between said second axis and said first axis.

2. The apparatus of claim 1, and wherein said spacing distance-changing means comprises journal means detachably secured on said frame means and constructed to rotatably support said column means on said second axis.

3. The apparatus of claim 2, and wherein said detachable journal means comprises a set of opposing bearing blocks detachably secured on said frame means and having bearing means to rotatably receive the opposite axial end portions of said column means and defining said second axis.

4. The apparatus of claim 2, and wherein said detachable journal means comprises a pair of opposing bearing blocks detachably secured on said frame means and having a plurality of radially spaced sets of bearing means located to rotatably support the axial end portions of said column means and defining correspondingly spaced selected locations of said second axis.

5. The apparatus of claim 1, and wherein said multi-layer helically coiled separation column means is mounted vertically and said first and second axes are vertical.

6. The apparatus of claim 1, and wherein said separation column means is provided with guide passage means located along said second axis and protectively receiving said flow tubes, and means to simultaneously rotate said column means around said second axis and revolve said frame means around said first axis at relative rates avoiding twisting of said flow tubes.

7. The apparatus of claim 1, and counterweight means detachably secured to said frame means opposite and in balancing relationship to said column means with respect to said first axis.

8. The apparatus of claim 1, and wherein said frame means includes a plurality of spaced parallel rigidly-connected plate members mounted for rotation around said first axis, and wherein said spacing distance-changing means comprising detachable journal means on an opposing pair of said plate members constructed to rotatably support said column means between said opposing pair for rotation on said second axis.

9. The apparatus of claim 8, and wherein said detachable journal means comprises respective bearing blocks detachably secured to the peripheral portions of said opposing pair of plate members and having bearing means to rotatably support the opposite axial end portions of said column means and defining said second axis.

10. The apparatus of claim 9, and wherein the bearing blocks are provided with radially spaced sets of bearing means located to rotatably support the axis end portions of said column means and defining correspondingly spaced selected positions of said second axis.

11. The apparatus of claim 8, and counterweight means detachably secured between said opposing pair of plate members and being in balancing relationship to said column means with respect to said first axis.

12. An apparatus for continuous countercurrent chromatography comprising a support, frame means rotatably mounted on said support for rotation on a first axis, multi-layer helically coiled separation column means rotatably mounted on said frame means for rotation on a second axis parallel to and spaced from said first axis, inlet and outlet flow tubes connected to the terminal ends of said multi-layer helically coiled column means, and means to simultaneously revolve said frame means around said first axis and rotate said multi-layer column means around said second axis.

* * * * *